US005780268A

United States Patent [19]
Coleman et al.

[11] Patent Number: 5,780,268
[45] Date of Patent: Jul. 14, 1998

[54] CHEMOKINE EXPRESSED IN A MIXED LYMPHOCYTE REACTION

[75] Inventors: Roger Coleman, Mountain View; Karl J. Guegler, Menlo Park; Jeffrey J. Seilhamer, Los Altos Hills, all of Calif.

[73] Assignee: Incyte Pharmaceuticals, Palo Alto, Calif.

[21] Appl. No.: 567,816

[22] Filed: Dec. 6, 1995

[51] Int. Cl.[6] .......................... C12N 15/19; C12N 15/85; C12N 5/06

[52] U.S. Cl. ...................... 435/69.5; 435/320.1; 435/325; 536/23.5

[58] Field of Search ...................... 536/23.5; 435/320.1, 435/240.2, 69.5, 325

[56] References Cited

PUBLICATIONS

Yoshida T. et al. "Molecular cloning of a novel C or gamma type chemokine, SCM-1." FEBS Letters 360: 155–159, Feb. 27, 1995.

Sarker G. et al. "Restriction-site PCR: A direct method of unknown sequence retrieval adjacent to a known locus by using universal primers." PCR Methods and Applications 2:318–322, 1993.

Sambrook J. et al. "Molecular Cloning: A Laboratory Manual." Cold Spring Harbor Laboratory Press, NY, pp. 17-1 to 17-44, 1989.

Kelner et al., "Lymphotactin: A Cytokine That Represents a New Class of Chemokine" *Science*, 266:1395–1399 (1994).

*Primary Examiner*—David T. Fox
*Assistant Examiner*—Amy J. Nelson
*Attorney, Agent, or Firm*—Lucy J. Billings

[57] ABSTRACT

The present invention provides nucleotide and amino acid sequences that identify and encode TMEC, a novel human lymphotactin expressed in T-cell mixed lymphocyte reaction (TMLR). The present invention also provides for polymerase chain reaction oligomers or hybridization probes for the detection of nucleotide sequences encoding TMEC or TMEC-like molecules, antisense molecules to the nucleotide sequences which encode TMEC, diagnostic tests based on TMEC encoding nucleic acid molecules, genetically engineered expression vectors and host cells for the production of purified TMEC, antibodies capable of binding specifically to TMEC, antagonists and inhibitors with specific binding activity for TMEC, and treatment methods.

4 Claims, 1 Drawing Sheet

1

CHEMOKINE EXPRESSED IN A MIXED LYMPHOCYTE REACTION

FIELD OF THE INVENTION

The present invention is in the field of molecular biology; more particularly, the present invention describes a nucleic acid sequence and an amino acid sequence for a novel human lymphotactin, a type of C chemokine.

BACKGROUND OF THE INVENTION

Chemokines are produced when the immune system responds to non-self antigens, such as invading microorganisms or antigens of an incompatible tissue type. One in vitro method for producing the immune response is produced by mixing T cells from antigenically distinct individuals and allowing them to react with one another in tissue culture in a mixed lymphocyte reaction (MLR). The T cell response which occurs in the MLR is called the T cell in a mixed lymphocyte reaction (TMLR). The MLR can be monitored qualitatively by observing blast formation or quantitatively on a scintillation counter (or equivalent) device by following the incorporation of tritiated thymidine during DNA synthesis. After mixing, the sensitized cells of the responding lymphocyte population become capable of killing cells of the stimulating population. Killer cells or cytotoxic T lymphocytes are produced, and their ability to perform cell mediated lympholysis (CML) can be monitored over a 4–8 hour time period by measuring chromium release from chromium-labeled target cells.

Investigations of MLR have provided information on graft rejection and its suppression and contributed to the understanding of the multiplicity of phenotypes that are important in histocompatibility. All body cells are equipped with antigens such as those of the major histocompatibility complex (MHC). The transplantation of tissues or organs between individuals with MHC incompatibilities quickly activates the recipient's immune system which then attempts to destroy the transplanted tissue or organ. Transplantation across minor histocompatibility loci generally induces a more indolent response. Physicians analyze the major and minor histocompatibility differences to predict the success of the graft and to adjust the aggressiveness of immunosuppressive therapy.

The T lymphocytes involved in the TMLR response originate in the bone marrow from pluripotent, hematopoietic stem cells. Precursor cells migrate via the blood to the thymus, where they differentiate into mature T lymphocytes. This differentiation is absolutely crucial in that it involves screening out those T cells which react with self molecules. Any immature or differentiating T cells which recognize and bind to native antigen-MHC complex become lymphoblastic. Such lymphoblastic cells are destroyed before they can be released into circulation. This screening is a continual, lifelong process which assures that all T cells entering the primary (vascular) or secondary (lymphoid) circulation tolerate the body's own ("self") tissues.

Homing receptors on the surfaces of the T cells govern their activity. For example, the cell-surface lectin, E-selectin, causes lymphocytes to adhere weakly to endothelial cells and slowly roll along their surface. Another example involves integrin which mediates stronger adhesion and directs lymphocytes from blood vessels to lymph nodes. Once activated, lymphocytes lose certain receptors and acquire new ones which lead them elsewhere, such as to a site of inflammation.

The second type of T cells, helper T cells are activated either by cytokines such as interleukin-1 (IL-1) or by signal molecules such as B7 and, in turn, activate other white blood cells via chemical signals. One class activates macrophages to destroy ingested microorganisms, while another stimulates B cells to produce antibodies. Helper T cells constitute about 75% of the total T cell population. They regulate the immune functions by producing and secreting lymphokines, IL-2, -3, -4, -5, and -6, which act specifically on other cells in the immune system and on bone marrow. For example, when IL-2 binds to its plasma membrane surface receptor, cytotoxic or helper T cells are stimulated to proliferate. Secreted signals also help B cells to proliferate and mature and, in some cases, to switch the class of antibody being produced. For example, secretion of IL-4 promotes IgE and IgG1 antibody production.

The physiology and disorders of T-cells are reviewed, inter alia, in Guyton AC (1991) Textbook of medical Physiology, W B Saunders Co, Philadelphia Pa.; Alberts B A et al (1994) Molecular Biology of the Cell, Garland Publishing Co, New York City; and Paul W E (1993) Fundamental Immunology, Raven Press, New York City.

Cytokines, and specifically chemokines, are frequently secreted at sites of inflammation. The chemokines are small polypeptides, generally about 70–100 amino acids in length, 8–11 kD in molecular weight and active over a 1–100 ng/ml concentration range. Initially, they were isolated and purified from inflamed tissues and characterized relative to their bioactivity. More recently, chemokines have been discovered through molecular cloning techniques and characterized by structural as well as functional analysis.

The chemokines are related through a four-cysteine motif which is based primarily on the spacing of the first two cysteine residues in the mature molecule. Most chemokines are assigned to either the C—C chemokines ($\alpha$) or the C—X—C chemokines ($\beta$). Although exceptions exist, the C—X—C chemokines generally activate neutrophils and fibroblasts while the C—C chemokines act on a more diverse group of target cells which include monocytes/macrophages, basophils, eosinophils, T lymphocytes and others. The known chemokines are synthesized by many diverse cell types as reviewed in Thomson A. (1994) The Cytokine Handbook, Academic Press, New York City.

A new class of chemokines, the C chemokines, has been proposed based on the lymphotactin molecule cloned from mouse (Kelner G et al (1994) Science 266:1395–99). Lymphotactin has similarity to both the C—C and the C—X—C chemokines, but it lacks two of the four cysteine residues that are characteristic of chemokines. In fact, only a $Cys_2$–$Cys_4$ disulfide bridge and the Phe and Tyr residues characteristic of the C—C family are present. In contrast to the other chemokines which are clustered on mouse chromosome 11, lymphotactin maps to the distal end of mouse chromosome 1. Finally, CD4$^+$—depleted and double negative (DN) thymocytes showed dose-dependent responses to mouse lymphotactin which appears to be specific for lymphocytes.

Current techniques for diagnosis of abnormalities in inflamed or diseased tissues mainly rely on observation of clinical symptoms or serological analyses of body tissues or fluids for hormones, polypeptides or various metabolites. Patients often manifest no clinical symptoms at early stages of disease or tumor development. Furthermore, serological analyses do not always differentiate between invasive diseases and genetic syndromes which have overlapping or very similar ranges. Thus, development of new diagnostic techniques comprising small molecules such as the expressed chemokines are important to provide for early and

3 accurate diagnoses and to give a better understanding of pathology at the molecular level. Current methods of treating such inflammations involve administration of steroids and other drugs with multiple side effects. New lymphotactin homologs can be used to develop more specific drugs with fewer side effects for controlling lymphocyte reactions.

The chemokine molecules are reviewed in Schall T J (1994) Chemotactic Cytokines: Targets for Therapeutic Development. International Business Communications, South-borough Mass., pp 180–270; and in Paul W E (1993) Fundamental Immunology. Raven Press, New York City, pp 822–26.

SUMMARY OF THE INVENTION

The present invention provides a polynucleotide with a unique nucleotide sequence which encodes a T cell mixed lymphocyte reaction expressed chemokine (TMEC) SEQ ID NO:2. The nucleotide sequence which encodes TMEC may be that shown in SEQ ID NO:1 between nucleotides 218 and 559. Alternatively, the nucleotide sequence may be any nucleotide sequence that encodes TMEC.

Additionally, the present invention provides for a polynucleotide with a nucleotide sequence encoding TMEC and additional control sequences for expression of TMEC. Such control sequences are shown in SEQ ID NO 1 between nucleotides 1 and 217 and between nucleotides 560 and 768.

Furthermore, the present invention provides cloning or expression vectors comprising a polynucleotide sequence encoding TMEC, and host cells or organisms transformed with expression vectors comprising the polynucleotide sequence.

The invention also provides a diagnostic test for conditions associated with the altered expression of TMEC, such as the activation of T cells, including the steps of testing a sample or an extract thereof with tmec DNA, fragments or oligomers thereof.

A further aspect of the invention includes the antisense DNA of tmec which is employed to inhibit translation of tmec mRNA.

Moreover, the present invention provides a method for the production and recovery of purified TMEC from host cells. Purified TMEC is effective for the production of antibodies against TMEC or to discover inhibitors of TMEC activity. Inhibitors, in particular, are employed as compounds specific for binding TMEC and controlling TMEC activity. The present invention also provides a method for treating conditions associated with T cell activation which comprises the administration of such inhibitors as a pharmaceutical composition in an effective dosage.

DETAILED DESCRIPTION OF THE INVENTION

Definitions

Figure 1:
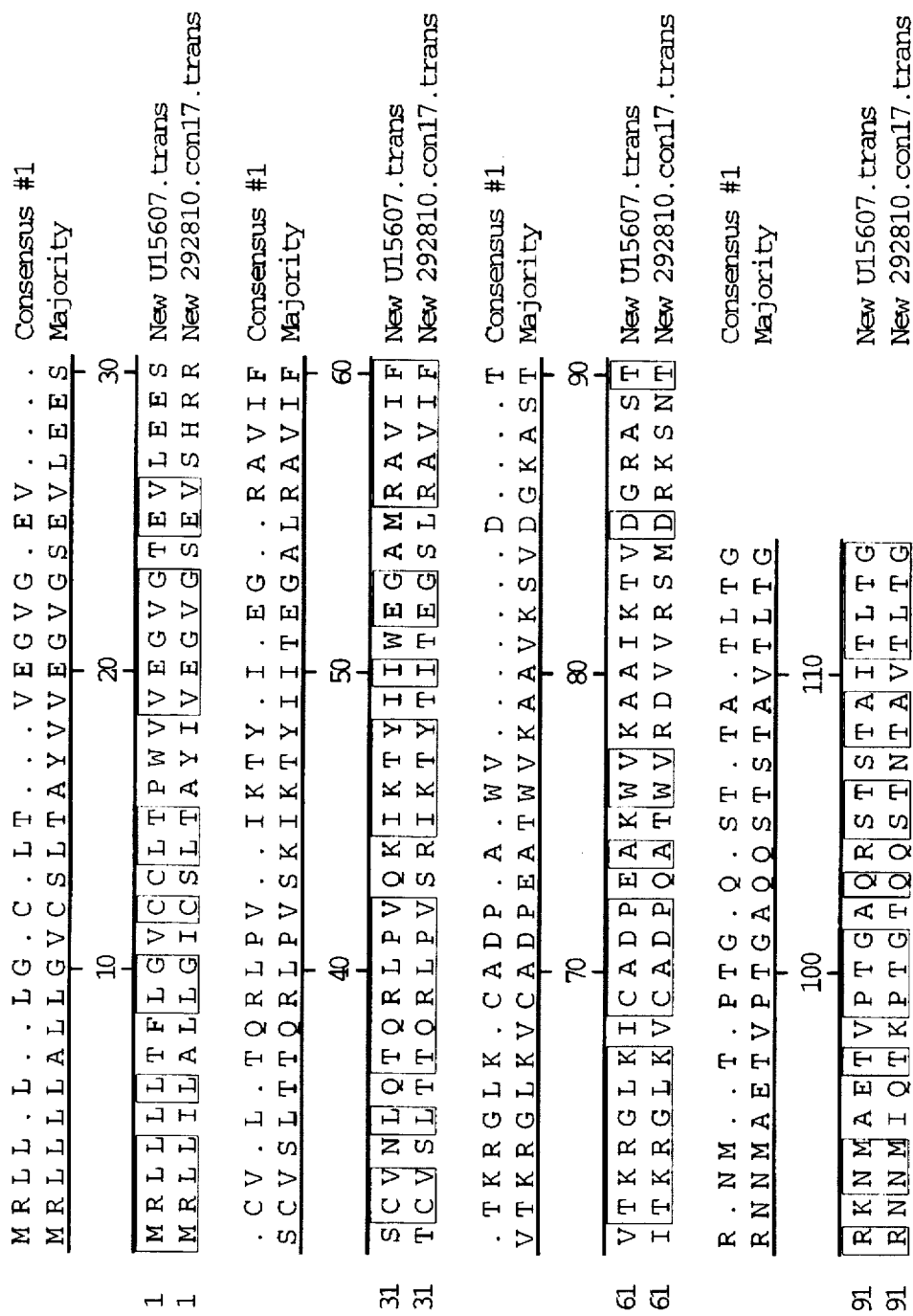
FIG. 1 shows the amino acid alignment of TMEC with mouse lymphotactin of the C chemokine family. Alignments shown were produced using the multisequence alignment program of DNASTAR™ software (DNASTAR Inc Madison Wis.).

The present invention provides a unique nucleotide sequence which encodes a T cell mixed lymphocyte reaction expressed chemokine (TMEC). TMEC is a human homolog of the mouse lymphotactin, which is a member of the C chemokine family. As used herein, the lower case letters, tmec, refer to a gene, cDNA or nucleic acid sequence while the upper case letters, TMEC, refer to a protein, polypeptide, peptide, oligopeptide, or amino acid sequence.

An "oligonucleotide" is a stretch of nucleotide residues which has a sufficient number of bases to be used as an oligomer, amplimer or probe in a polymerase chain reaction (PCR). Oligonucleotides are prepared from genomic or cDNA sequences and are used to amplify, confirm, or reveal the presence of an identical or similar DNA or RNA in a particular cell or tissue. Oligonucleotides or oligomers comprise portions of a DNA sequence having at least about 10 nucleotides and as many as about 50 nucleotides, preferably about 15 to 30 nucleotides.

"Probes" are nucleic acid sequences of variable length, preferably between at least about 10 and as many as about 6,000 nucleotides, depending on use. They are useful in the detection of identical, similar, or complementary nucleic acid sequences. Longer length probes are highly specific, but slow to hybridize. Shorter length probes are inexpensive and quick to hybridize, but must be carefully designed to have specificity. Single- or double-stranded probes may be either chemically synthesized or obtained and/or modified from naturally occurring or recombinant sequences.

"Reporter" or "label" molecules are chemical moieties used for labelling a nucleic or amino acid sequence. They include, but are not limited to, radionuclides, enzymes, fluorescent, chemiluminescent, or chromogenic agents. Reporter molecules associate with, establish the presence of, permit quantification of a particular nucleic or amino acid sequence, or can be used therapeutically.

A "portion" or "fragment" of a polynucleotide or nucleic acid comprises all or any part of the nucleotide sequence having fewer nucleotides than about 6 kb, preferably fewer than about 1 kb, which can be used as a probe, can be therapeutically active, or can be used to synthesize a polypeptide fragment. Such probes may be labelled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Recombinant nucleotide variants" are polynucleotides which encode a protein. They may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively. Recombinant nucleotide variants also include polynucleotides with the necessary nucleic acid substitutions, insertions and/or deletions to produce the recombinant polypeptide variants (described below).

"Linkers" are synthesized palindromic oligomers which create internal restriction endonuclease sites for ease of cloning the genetic material of choice into various vectors.

The term "chimeric molecule", as used herein, refers to polynucleotides or polypeptides which are created by combining one or more nucleotide sequences of this invention with additional nucleic acid sequence(s). Such combined sequences may be introduced into an appropriate vector and expressed to give rise to a chimeric polypeptide. Examples of useful chimeric polypeptides are those with changes in cellular location, distribution, ligand-binding affinities, interchain affinities, degradation/turnover rate, signalling, etc.

"Active" describes a molecular state of a molecule which is capable of initiating some process or of carrying out some role. In this patent it specifically refers to those forms, fragments, or domains of an amino acid sequence which display biologic and/or immunogenic properties characteristic of the naturally occurring polypeptide.

"Naturally occurring TMEC" refers to a polypeptide produced by cells which have not been genetically engineered or which have been genetically engineered to produce the same sequence as that naturally produced. Specifically contemplated are various polypeptides which arise from post-translational modifications. Such modifications of the polypeptide include but are not limited to acetylation, carboxylation, glycosylation, phosphorylation, lipidation and acylation.

"Derivative" refers to those polypeptides which have been chemically modified by such techniques as ubiquitination, labelling (see above), pegylation (derivatization with polyethylene glycol), and chemical insertion, deletion, or substitution of amino acids. It comprises substitutions of amino acids such as ornithine which do not normally occur in human proteins.

"Recombinant polypeptide variant" refers to any polypeptide which differs from naturally occurring TMEC by amino acid insertions, deletions and/or substitutions, created using recombinant DNA techniques. Guidance in determining which amino acid residues may be replaced, added or deleted without abolishing characteristics of interest may be found by comparing the sequence of TMEC with that of related polypeptides and minimizing the number of amino acid changes in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are additions or eliminations of amino acids from polypeptides. They typically fall in the range of about 1 to 5 amino acids. The variation allowed in a particular amino acid sequence may be experimentally determined by producing the peptide synthetically or by systematically making insertions, deletions, or substitutions of nucleotides in the tmec sequence using recombinant DNA techniques.

A "signal or leader sequence" is a short amino acid sequence which directs, or can be used to direct, the polypeptide through a membrane of a cell. Such a sequence may be naturally present on the polypeptides of the present invention or provided from heterologous sources and added to the polypeptide by recombinant DNA techniques.

An "oligopeptide" is a short stretch of amino acid residues and may be expressed from an oligonucleotide. It may be considerably shorter than and the same length as a "fragment," "portion," or "segment" of a polypeptide. An oligopeptide comprises a stretch of amino acid residues of at least about 5 amino acids and often about 17 or more amino acids, typically at least about 9 to 13 amino acids, and of sufficient length to display biologic and/or immunogenic activity.

An "inhibitor" is a substance which retards or prevents a chemical or physiological reaction or response. Common inhibitors include but are not limited to antisense molecules, antibodies, antagonists and derivatives. Inhibitors differ from recombinant variants in that they do not display the same reactivity but diminish or block the activity of the natural or derivative compound.

A "standard" is a quantitative or qualitative measurement for comparison. Preferably, it is based on a statistically appropriate number of samples and is created to use as a basis of comparison when performing diagnostic assays, running clinical trials, or following patient treatment profiles. The samples of the standard may be normal or similarly abnormal.

"Animal" as used herein may be defined to include human, domestic (cats, dogs, etc.), agricultural (cows, fish, horses, sheep, chickens, etc) or test species (frogs, mouse, rat, rabbit, etc).

"Conditions which cause activation of T cells" include viral, bacterial, fungal or parasitic infections; mechanical injury associated with trauma; autoimmune or hereditary diseases such as AIDS, allergies, asthma and rheumatoid arthritis; cancers and infiltrative diseases such as carcinomas, leukemias and lymphomas; or other physiologic and pathologic problems which trigger uncontrolled proliferation of T lymphocytes.

Since the list of technical and scientific terms cannot be all encompassing, any undefined terms shall be construed to have the same meaning as is commonly understood by one of ordinary skill in the art to which this invention belongs. Furthermore, the singular forms "a", "an" and "the" include plural referents unless the context clearly dictates otherwise. For example, reference to a "high-fidelity enzyme" includes mixtures of such enzymes and any other enzymes fitting the stated criteria, and reference to "the method" includes reference to one or more methods for doing the same thing, which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

DESCRIPTION OF THE INVENTION

The present invention provides a nucleotide sequence, first identified in Incyte Clone 292810. Incyte Clone 292810 was isolated from the TMLR cDNA library described in co-pending patent application entitled "Polynucleotides and Polypeptides Derived from T cells in a Mixed Lymphocyte Reaction (TMLR)", Ser. No. 08/440,817, filed May 15, 1995, hereby incorporated by reference.

The nucleotide sequence uniquely identifies a novel chemokine, TMLR expressed chemokine or TMEC. TMEC belongs to the family of C chemokines. Because TMEC is specifically expressed in activated T cells, the nucleic acids (tmec), polypeptides (TMEC) and antibodies to TMEC are useful in diagnostic assays which survey for increased chemokine production. Excessive expression of TMEC is associated with the activation of T lymphocytes which respond to C chemokines and can result in the production of abundant proteases and other molecules which can lead to tissue damage or destruction. Therefore, a diagnostic test for excessive expression of TMEC can accelerate identification and proper treatment of abnormal conditions which cause activation of T cells.

The purified nucleic acid sequence for tmec has numerous applications in techniques known to those skilled in the art of molecular biology. These techniques include its use as a hybridization probe, for chromosome and gene mapping, in PCR technologies, in the production of sense or antisense nucleic acids, in screening for new therapeutic molecules, etc. These examples are well known and are not intended to be limiting. Furthermore, tmec may be used in molecular biology techniques that have not yet been developed, provided the new techniques rely on properties of nucleotide sequences that are currently known such as the triplet genetic code, specific base pair interactions, etc.

As a result of the degeneracy of the genetic code, a multitude of chemokine-encoding nucleotide sequences may be produced and some of these will bear only minimal homology to the endogenous sequence of any known and naturally occurring chemokine. This invention has specifically contemplated each and every possible variation of nucleotide sequence that could be made by selecting combinations based on possible codon choices. These combinations are made in accordance with the standard triplet genetic code as applied to the nucleotide sequence of naturally occurring lymphotactins, and all such variations are to be considered as being specifically disclosed.

Although the tmec nucleotide sequence and its derivatives or variants are preferably capable of identifying the nucleotide sequence of the naturally occurring TMEC under optimized conditions, it may be advantageous to produce tmec nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the tmec nucleotide sequence without altering the encoded amino acid sequence include the production of RNA transcripts having more desirable properties, such as a longer half-life, than transcripts produced from the naturally occurring sequence.

Nucleotide sequences for tmec may be joined to a variety of other nucleotide sequences by means of well established recombinant DNA techniques (Sambrook J et al (1989) Molecular Cloning: A Laboratory Manual, Cold Spring Harbor Laboratory, Cold Spring Harbor N.Y.; or Ausubel FM et al (1989) Current Protocols in Molecular Biology, John Wiley & Sons, New York City). Useful sequences for joining to tmec include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

PCR as described in U.S. Pat. Nos. 4,683,195; 4,800,195; and 4,965,188 provides additional uses for oligonucleotides based upon the tmec nucleotide sequence. Such oligomers are generally chemically synthesized, but they may be of recombinant origin or a mixture of both. Oligomers may comprise two nucleotide sequences employed under optimized conditions for tissue specific identification or diagnostic use. The same two oligomers, nested sets of oligomers, or even a degenerate pool of oligomers may be employed under less stringent conditions for identification and/or quantitation of closely related DNA or RNA sequences.

Full length genes may be cloned utilizing partial nucleotide sequence and various methods known in the art. "Restriction-site PCR" is a direct method (Gobinda et al (1993) PCR Methods Applic 2:318–22) which uses universal primers to retrieve unknown sequence adjacent to a known locus. First, genomic DNA is amplified in the presence of high fidelity enzymes, a primer adjacent to linker, and a primer specific adjacent to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR (Triglia T et al (1988) Nucleic Acids Res 16:8186) is the first method to report successful acquisition of unknown sequences starting with primers based on a known region. The method uses several restriction enzymes to generate a suitable fragment in the known region of a gene. The fragment is then circularized by intramolecular ligation and used as a PCR template. Divergent primers are designed to prime outward from the known region and multiple rounds of restriction enzyme digestions and ligations are necessary.

Capture PCR (Lagerstrom M et al (1991) PCR Methods Applic 1:111–19) is a method for PCR amplification of DNA fragments adjacent to a known human sequence in a yeast artificial chromosome (YAC). Capture PCR also requires multiple restriction enzyme digestions and ligations to place an engineered double-stranded sequence into an unknown portion of the DNA molecule before PCR. This method allows the restriction and ligation reactions to be carried out simultaneously and further requires extension, immobilization, two rounds of PCR and purification prior to sequencing.

Walking PCR (Parker J D et al (1991) Nucleic Acids Res 19:3055–60) is a method for targeted gene walking for the retrieval of unknown sequence. It requires oligomer- extension assay followed by gel purification and identification of the desired fragment prior to sequencing.

A new method which employs XL-PCR (Perkin-Elmer, Foster City, Calif.) amplifies and extends partial nucleotide sequence into long pieces of DNA. This method was developed to allow a single researcher to process multiple genes (up to 20 or more) at a time and to obtain an extended (possibly full-length) sequence within 6–10 days. This new method replaces methods which use labelled probes to screen plasmid libraries and allow one researcher to process only about 3–5 genes in 14–40 days.

In the first step, which can be performed in about two days, any two of a plurality of primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones.

If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg MD). The cDNA library may have been prepared with oligo (dT) or random priming. Random primed libraries are preferred in that they will contain more sequences which contain 5' ends of genes. A randomly primed library may be particularly useful if an oligo (dT) library does not yield a complete gene. It must be noted that the larger and more complex the protein, the less likely it is that the complete gene will be found in a single plasmid.

Another aspect of the subject invention is to provide for a tmec hybridization probe which is capable of hybridizing with naturally occurring nucleotide sequences for tmec. The stringency of the hybridization conditions will determine whether the probe identifies only the native lymphotactin or sequence of closely related C chemokine molecules. If a degenerate tmec sequence of the subject invention is used for the detection of related C chemokine sequences, it should preferably contain at least 50% of the nucleotides of the sequence presented herein. Hybridization probes may be derived from the nucleotide sequence of the SEQ ID NO:1, or from surrounding or included genomic sequences comprising untranslated regions such as promoters, enhancers and introns. Such hybridization probes may be labelled with appropriate reporter molecules.

Means for producing specific hybridization probes for tmec include oligolabelling, nick translation, end-labelling or PCR amplification using a labelled nucleotide. Alternatively, the cDNA sequence may be cloned into a vector for the production of mRNA probe. Such vectors are known in the art, are commercially available, and may be used to synthesize RNA probes in vitro by addition of an appropriate RNA polymerase such as T7, T3 or SP6 and labelled nucleotides. A number of companies which develop molecular biology products (such as Pharmacia Biotech, Piscataway N.J.; Promega, Madison Wis.; USB, Cleveland Ohio, etc.) supply commercial kits and protocols for these various procedures.

It is also possible to produce a DNA sequence, or portions thereof, entirely by synthetic chemistry. Sometimes the source of information for producing this sequence comes from a known homologous sequence from a closely related organism. After synthesis, the nucleic acid sequence can be used alone or joined with other sequence(s) and inserted into one of the many available DNA vectors and their respective host cells using techniques well known in the art. Moreover, synthetic chemistry may be used to introduce specific mutations into the nucleotide sequence. Alternatively, a portion of sequence in which a mutation is desired can be synthesized and recombined with a portion of an existing genomic or recombinant sequence.

The nucleotide sequence for tmec can be used in an assay to detect inflammation or disease associated with abnormal levels of TMEC expression. The cDNA can be labeled by methods known in the art and added to a fluid, cell or tissue sample from a patient under hybridizing conditions. After an incubation period, the sample is washed with a compatible fluid which optionally contains a reporter molecule. After the compatible fluid is rinsed off, the reporter molecule is quantitated and compared with a standard as previously defined. If lymphotactin expression is significantly different from standard expression, the assay indicates inflammation or disease.

This same assay, combining a sample with the nucleotide sequence, is applicable in evaluating the efficacy of a particular therapeutic treatment regime. It may be used in animal studies, in clinical trials, or in monitoring the treatment of an individual patient. First, standard expression must be established for use as a basis of comparison. Second, samples from the animals or patients affected by the disease are combined with the nucleotide sequence to evaluate the deviation from the standard or normal profile. Third, an existing therapeutic agent is administered, and a treatment profile is generated. The assay is evaluated to determine whether the profile progresses toward or returns to the standard pattern. Successive treatment profiles may be used to show the efficacy of treatment over a period of several days or several months.

The tmec nucleotide sequence can also be used to generate probes for mapping the native gene. The sequence may be mapped to a particular chromosome or to a specific region of the chromosome using well known techniques. These include in situ hybridization to chromosomal spreads (Verma et al (1988) Human Chromosomes: A Manual of Basic Techniques, Pergamon Press, New York City), flow-sorted chromosomal preparations, or artificial chromosome constructions such as YACs, bacterial artificial chromosomes (BACs), bacterial Pi constructions or single chromosome cDNA libraries.

In situ hybridization of chromosomal preparations and physical mapping techniques such as linkage analysis using established chromosomal markers are invaluable in extending genetic maps. Examples of genetic maps can be found in the 1994 Genome Issue of Science (265:1981f). Often the placement of a gene on the chromosome of another mammalian species may reveal associated markers even if the number or arm of a particular human chromosome is not known. New partial nucleotide sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent genes for further investigation. The nucleotide sequences of the subject invention may also be used to detect differences in the chromosomal location of nucleotide sequences due to translocation, inversion, etc. between normal and carrier or affected individuals.

The tmec nucleotide sequence may be used to produce an amino acid sequence using well known methods of recombinant DNA technology (Goeddel (1990, Gene Expression Technology, Methods and Enzymology, Vol 185, Academic Press, San Diego Calif.). The amino acid sequence or peptide may be expressed in a variety of host cells, either prokaryotic or eukaryotic. Host cells may be from the same species from which the nucleotide sequence was derived or from a different species. Advantages of producing an amino acid sequence or peptide by recombinant DNA technology include obtaining adequate amounts for purification and the availability of simplified purification procedures.

Cells transformed with tmec may be cultured under conditions suitable for the expression and recovery of peptide from cell culture. The peptide produced by a recombinant cell may be secreted or may be contained intracellularly depending on the sequence itself and/or the vector used. In general, it is more convenient to prepare recombinant proteins in secreted form, and this is accomplished by ligating tmec to a recombinant nucleotide sequence which directs its movement through a particular prokaryotic or eukaryotic cell membrane. Other chimeric constructions may join tmec to nucleotide sequence encoding a polypeptide domain which will facilitate protein purification (Kroll D J et al (1993) DNA Cell Biol 12:441–53).

Direct peptide synthesis using solid-phase techniques (Stewart et al (1969) Solid-Phase Peptide Synthesis, W H Freeman Co. San Francisco Calif.; Merrifield J (1963) J Am Chem Soc 85:2149–2154) is an alternative to recombinant or chimeric peptide production. Automated synthesis may be achieved, for example, using Applied Biosystems 431A Peptide Synthesizer (Foster City Calif.) in accordance with the instructions provided by the manufacturer. Additionally the TMEC sequence or any part thereof may be mutated during direct synthesis and, if desired, combined using chemical methods with another amino acid sequence(s).

Although an amino acid sequence or oligopeptide used for antibody induction does not require biological activity, it must be immunogenic. TMEC used to induce specific antibodies may have an amino acid sequence consisting of at least five amino acids and preferably at least 10 amino acids. Short stretches of amino acid sequence may be fused with those of another protein such as keyhole limpet hemocyanin, and the chimeric peptide used for antibody production. Alternatively, the oligopeptide may be of sufficient length to contain an entire domain.

Antibodies specific for TMEC may be produced by inoculation of an appropriate animal with an antigenic fragment of the peptide. An antibody is specific for TMEC if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (Orlandi R et al (1989) PNAS 86:3833–3837, or Huse W D et al (1989) Science 256:1275–1281), or the in vitro stimulation of lymphocyte populations.

Current technology (Winter G and Milstein C (1991) Nature 349:293–299) provides for a number of highly specific binding reagents based on the principles of antibody formation. These techniques may be adapted to produce molecules which specifically bind TMEC. Antibodies or other appropriate molecules generated against a specific immunogenic peptide fragment or oligopeptide can be used in Western analysis, enzyme-linked immunosorbent assays (ELISA) or similar tests to establish the presence of or to quantitate amounts of TMEC active in normal, diseased, or therapeutically treated cells or tissues.

An additional embodiment of the subject invention is the use of TMEC specific antibodies, inhibitors, receptors or their analogs as bioactive agents to treat inflammation or conditions which cause activation of T cells including, but not limited to viral, bacterial, fungal or parasitic infections; mechanical injury associated with trauma; autoimmune or hereditary diseases such as AIDS, allergies, asthma and rheumatoid arthritis; cancers and infiltrative diseases such as carcinomas, leukemias and lymphomas; or other physiologic and pathologic problems associated with uncontrolled proliferation of T lymphocytes.

Bioactive compositions comprising agonists, antagonists, receptors or inhibitors of TMEC may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving chemokine production and function.

The examples below are provided to illustrate the subject invention. These examples are provided by way of illustration and are not included for the purpose of limiting the invention.

EXAMPLES

I cDNA Library Construction

The peripheral blood T-lymphocytes used to create the TMLR cDNA library were obtained from two healthy Caucasian adult male employees of Incyte Pharmaceuticals Inc. This library represents a mixture of allogeneically stimulated human cell/macrophage populations obtained from Ficoll/Hypaque purified buffy coats. The cells from two different donors (not typed for HLA alleles) were incubated at a density of $1 \times 10^6$/ml, cultured in this instance for 4 days in DME at 10% human serum, washed in PBS, scraped and lyzed immediately in buffer containing guanidinium isothiocyanate. The lysate was centrifuged over a CsCl cushion, ethanol precipitated, resuspended in water and DNase treated for 15 min at 37° C. The RNA was extracted with phenol chloroform and precipitated with ethanol. Total RNA was sent to Stratagene (La Jolla Calif.).

Stratagene prepared the cDNA library using oligo (dT) priming. Synthetic adapter oligonucleotides were ligated onto the cDNA molecules enabling them to be inserted into the Uni-ZAP™ vector system (Stratagene). This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into E. coli host strain XL1-Blue® (Stratagene). The high transformation efficiency of this bacterial strain increases the probability that the cDNA library will contain rare, under-represented clones. Alternative unidirectional vectors might include, but are not limited to, pcDNAI (Invitrogen, San Diego Calif.) and pSHlox-1 (Novagen, Madison Wis.).

II Isolation of cDNA Clones

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

Phagemid DNA was also purified using the QIAWELL-8 Plasmid Purification System (QIAGEN Inc, Chatsworth, Calif.). This product provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin and prepared for DNA sequencing and other analytical manipulations.

An alternate method of purifying phagemid has recently become available. It utilizes the Miniprep Kit (Catalog No. 77468, Advanced Genetic Technologies Corp, Gaithersburg, Md.). This kit is in the 96-well format and provides enough reagents for 960 purifications. Each kit is provided with a recommended protocol, which has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 µl of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

III Sequencing of cDNA Clones

The cDNA inserts from random isolates of the TMLR library were sequenced in part. Methods for DNA sequencing are well known in the art. Conventional enzymatic methods employed DNA polymerase, SEQUENASE® (US Biochemical Corp, Cleveland Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Applied Biosystems Catalyst 800 and the 377 or 373 DNA sequencer.

IV Homology Searching of cDNA Clones and Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul SF (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. While BLAST effectively identifies matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Identification and Full Length Sequencing of the Gene

During the analysis of TMLR partial cDNA sequences, Incyte Clone 292810 was identified as containing at least a portion of the tmec sequence which is homologous to mouse lymphotactin, a C chemokine. Clone 292810 was amplified and resequenced and found to contain most of coding sequence for the putatative lymphotactin (residues 25 to 114). To obtain the full-length sequence, two oligonucleotide primers were synthesized based on the n tmec sequence and were used for PCR amplification to screen the Gibco/BRL SUPERSCRIPT® Human Leukocyte Library (Cat. No. 10421-014, Life Technologies, Gaithersburg Md.) to identify clones containing additional tmec sequence. The full-length tmec sequence, including 5'- and 3'-untranslated regions are shown in SEQ ID NO:1. The tmec coding sequence is shown in SEQ ID NO:1 starts at nucleotide 218 and ends at nucleotide 559. The sequence for the 3' primer is the sequence of SEQ ID NO:1 starting at nucleotide 569 and ending at nucleotide 592. The sequence for the 5' primer is the complementary sequence of SEQ ID NO:1 starting at nucleotide 367 and ending at nucleotide 388.

The complete nucleotide sequence for tmec was translated, and the in-frame translation is shown in SEQ ID NOs 2 and 3. All three possible predicted translations of the sequence were searched against protein databases such as SwissProt and PIR. FIG. 1 shows the alignment between the TMEC and mouse lymphotactin amino acid sequences. The TMEC amino acid sequence possesses 61% homology with the mouse lympotactin sequence. If both identical amino acid and conservative amino acid substitutions are considered, the degree of homology increases to about 80%. TMEC includes the two conserved cysteines (residues 32 and 69), phenylalanine (residue 60) and tyrosine (residue 48), but lacks the other two cysteine residues characteristic of the C—C and C—X—C chemokine families. Therefore, TMEC is a new member of the C chemokine family.

VI Sense or Antisense Molecules

Knowledge of the correct cDNA sequence of tmec or any part thereof will enable its use as a tool in sense or antisense technologies for the investigation of gene function. oligonucleotides, from genomic or cDNAs, comprising either the sense or the antisense strand of the cDNA sequence can be used in vitro or in vivo to inhibit expression. Such technology is now well known in the art, and oligonucleotides or other fragments can be designed from various locations along the sequences. The gene of interest can be turned off in the short term by transfecting a cell or tissue with expression vectors which will flood the cell with sense or antisense sequences until all copies of the vector are disabled by endogenous nucleases. Stable transfection of appropriate germ line cells or a zygote with a vector containing the fragment will produce a transgenic organism (see for example, U.S. Pat. No. 4,736,866, 12 Apr. 1988), whose cells produce enough copies of the sense or antisense sequence to significantly compromise or entirely eliminate normal activity of the lymphotactin gene. Frequently, the function of a gene can be ascertained by observing behaviors such as lethality, loss of a physiological pathway, changes in morphology, etc. at the intracellular, cellular, tissue or organismal level.

In addition to using fragments constructed to interrupt transcription of the open reading frame, modifications of gene expression can be obtained by designing antisense sequences to promoters, enhancers, introns, or even to trans-acting regulatory genes. Similarly, inhibition can be achieved using Hogeboom base-pairing methodology, also known as "triple helix" base pairing.

VII Expression of TMEC

Expression of TMEC may be accomplished by subcloning the cDNAs into appropriate expression vectors and transfecting the vectors into appropriate expression hosts. In this particular case, the cloning vector previously used for the generation of the tissue library also provides for direct expression of the included tmec sequence in *E. coli*. Upstream of the cloning site, this vector contains a promoter for β-galactosidase, followed by sequence containing the amino-terminal Met and the subsequent seven residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 5 to 15 residues which correspond to linker, and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The tmec cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequences.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced TMEC can be recovered from the conditioned medium and analyzed using chromatographic methods known in the art.

VIII Isolation of Recombinant TMEC

TMEC may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen, San Diego Calif.) between the purification domain and the tmec sequence may be useful to facilitate expression of TMEC.

IX Production of TMEC Specific Antibodies

Two approaches are utilized to raise antibodies to TMEC, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of TMEC, as deduced from translation of the cDNA, is analyzed to determine regions of high immunogenicity. Oligopeptides comprising appropriate hydrophilic regions generarated by a hydrophobicity plot are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N- hydroxysuccinimide ester (MBS; Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled TMEC to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled TMEC, 1 mg/ml. Clones producing antibodies will bind a quantity of labeled TMEC which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$ $M^{-1}$, preferably $10^9$ to $10^{10}$ or stronger, will typically be made by standard procedures as described in Harlow and Lane (1988) Antibodies: A Laboratory Manual, Cold Spring Harbor Laboratory, Cold Spring Harbor N.Y.; and in Goding (1986) Monoclonal Antibodies: Principles and Practice, Academic Press, New York City, both incorporated herein by reference.

X Diagnostic Test Using TMEC Specific Antibodies

Particular TMEC antibodies are useful for the diagnosis of prepathologic conditions, as well as chronic or acute diseases which are characterized by differences in the amount or distribution of TMEC. To date, TMEC has only been found in the human TMLR library and is thus specific for abnormalities or pathologies which affect the TMLR.

Diagnostic tests for TMEC include methods utilizing the antibody and a label to detect TMEC in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound TMEC, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on TMEC is preferred, but a competitive binding assay may be employed. These assays are described, among other places, in Maddox, Del. et al (1983, J Exp Med 158:1211).

XI Purification of Native TMEC Using Specific Antibodies

Native or recombinant TMEC can be purified by immunoaffinity chromatography using antibodies specific for TMEC. In general, an immunoaffinity column is constructed by covalently coupling the anti-TMEC antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of TMEC by preparing a fraction from cells containing TMEC in a soluble form. This preparation is derived by solubilization of the whole cell or of a subcellular fraction obtained via differential centrifugation by the addition of detergent or by other methods well known in the art. Alternatively, soluble TMEC containing a signal sequence may be secreted in useful quantity into the medium in which the cells are grown.

A soluble TMEC-containing preparation is passed over the immunoaffinity column, and the column is washed under conditions that allow the preferential absorbance of chemokines (eg. high ionic strength buffers in the presence of detergent). Then, the column is eluted under conditions that disrupt antibody/chemokine binding (e.g., a buffer of pH 2-3 or a high concentration of a chaotrope such as urea or thiocyanate ion), and TMEC is collected.

XII TMEC Induced Chemotaxis or Cell Activation

The chemotactic activity of TMEC is measured in 48-well microchemotaxis chambers (Falk W R et al (1980) J Immunol Methods 33:239). In each well, two compartments are separated by a filter that allows the passage of cells in response to a chemical gradient. Cell culture medium such as RPMI 1640 (Sigma, St. Louis Mo.) containing the expressed chemokine is placed on one side of a filter, usually polycarbonate, and cells suspended in the same media are placed on the opposite side of the filter. Sufficient incubation time is allowed for the cells to traverse the filter in response to the concentration gradient across the filter. Filters are recovered from each well, and cells adhering to the side of the filter facing the chemokine are typed and quantified.

The specificity of the chemoattraction is determined by performing the chemotaxis assay on specific populations of cells. First, blood cells obtained from venipuncture are fractionated by density gradient centrifugation and the chemotactic activity of TMEC is tested on enriched populations of neutrophils, peripheral blood mononuclear cells, monocytes and lymphocytes. optionally, such enriched cell populations are further fractionated using CD8+ and CD4+ specific antibodies for negative selection of CD4+ and CD8+ enriched T-cell populations, respectively.

Another assay elucidates the chemotactic effect of TMEC on activated T-cells. There, unfractionated T-cells or fractionated T-cell subsets are cultured for 6 to 8 hours in tissue culture vessels coated with CD-3 antibody. After this CD-3 activation, the chemotactic activity of TMEC is tested as described above. Many other methods for obtaining enriched cell populations are known in the art.

Some chemokines also produce a non-chemotactic cell activation of neutrophils and monocytes. This is tested via standard measures of neutrophil activation such as actin polymerization, increase in respiratory burst activity, degranulation of the azurophilic granule and mobilization of $Ca^{++}$ as part of the signal transduction pathway. The assay for mobilization of Ca++ involves preloading neutrophils with a fluorescent probe whose emission characteristics have been altered by Ca++ binding. When the cells are exposed to an activating stimulus, Ca++ flux is determined by observation of the cells in a fluorometer. The measurement of Ca++ mobilization has been described in Grynkievicz G et al (1985) J Biol Chem 260:3440, and McColl S et al (1993) J Immunol 150:4550–4555, incorporated herein by reference.

Degranulation and respiratory burst responses are also measured in monocytes (Zachariae COC et al. (1990) J Exp Med 171: 2177–82). Further measures of monocyte activation are regulation of adhesion molecule expression and cytokine production (Jiang Y et al (1992) J Immunol 148: 2423–8). Expression of adhesion molecules also varies with lymphocyte activation (Taub D et al (1993) Science 260: 355–358).

XIII Drug Screening

This invention is particularly useful for screening compounds by using TMEC polypeptide or binding fragments thereof in any of a variety of drug screening techniques. The chemokine polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between TMEC and the agent being tested. Alternatively, one can examine the diminution in complex formation between TMEC and its target cell, monocyte, etc. caused by the agent being tested.

Thus, the present invention provides methods of screening for drugs or any other agents which can affect inflammation and disease. These methods comprise contacting such an agent with a TMEC polypeptide or fragment thereof and assaying (i) for the presence of a complex between the agent and the TMEC polypeptide or fragment, or (ii) for the presence of a complex between the TMEC polypeptide or fragment and the cell, by methods well known in the art. In such competitive binding assays, the chemokine polypeptide or fragment is typically labeled. After suitable incubation, free TMEC polypeptide or fragment is separated from that present in bound form, and the amount of free or uncomplexed label is a measure of the ability of the particular agent to bind to TMEC or to interfere with the TMEC and agent complex.

Another technique for drug screening provides high throughput screening for compounds having suitable binding affinity to the TMEC polypeptide and is described in detail in European Patent Application 84/03564, published on Sept. 13, 1984, incorporated herein by reference. Briefly stated, large numbers of different small peptide test compounds are synthesized on a solid substrate, such as plastic pins or some other surface. The peptide test compounds are reacted with TMEC polypeptide and washed. Bound TMEC polypeptide is then detected by methods well known in the art. Purified TMEC can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding TMEC specifically compete with a test compound for binding to chemokine polypeptides or fragments thereof. In this manner, the antibodies can be used to detect the presence of any peptide which shares one or more antigenic determinants with TMEC.

XIV Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural inform ation is used to design analogous chemokine-like molecules or to identify efficient inhibitors. Useful examples of rati onal drug design may include molecul es which have improved activity or stability as shown by Braxton S and Wells J A (1992 Biochemistry 31:7796–7801) or which act as inhibitors, agonists, or antagonists of native peptides as shown by Athauda SB et al (1993 J Biochem 113:742–746), incorporated herein by reference.

It is als o possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the TMEC amino acid sequence provided herein will provide guidance to those employing computer modeling techniques in place of or in addition to x-ray crystallography.

xv Identification of TMEC Receptors

Purified TMEC is useful for characterization and purification of spec ific cell surface receptor s and other binding molecules. Cells 30 which respond to TMEC by chemotaxis or other specific resp onses are likely to express a receptor for TMEC. Radioactive labels may be incorporated into TMEC by various methods known in the art. A preferred embodiment is the labeling of primary amino gr oups in TMEC with $^{125}I$ Bolton-Hunter reagent (Bolton, A E and Hunter, W M (1973) Biochem J 133:529), which has been used to label other chemokines without concomitant loss of biological activity (Hebert C A et al (1991) J Biol Chem 266:18989–94; McColl S et al (1993) J Immunol 150:4550–4555). Receptor-bearing cells are incubated with the labeled chemokine molecule. The cells are then washed to removed unbound chemokine, and receptor-bound labeled molecule is quantified. The data obtained using different concentrations of TMEC are used to calculate values for the number and affinity of receptors.

Labeled TMEC is also useful as a reagent for purification of its specific receptor. In one embodiment of affinity purification, the chemokine is covalently coupled to a chromatography column. Receptor-bearing cells are extracted, and the extract is passed over the column. The receptor binds to the column by virtue of its biological affinity for TMEC. The receptor is recovered from the column and subjected to N-terminal protein sequencing. This amino acid sequence is then used to design degenerate oligonucleotide probes for cloning the receptor gene.

In an alternate method, mRNA is obtained from receptor-bearing cells and made into a cDNA library. The library is transfected into a population of cells, and those cells expressing the receptor are selected using fluorescently labeled TMEC. The TMEC specific receptor is identified by recovering and sequencing recombinant DNA from highly labeled cells.

In another alternate method, antibodies are raised against the surface of receptor-bearing cells, specifically monoclonal antibodies. The monoclonal antibodies are screened to identify those which inhibit the binding of labeled TMEC. These monoclonal antibodies are then used in affinity purification or expression cloning of the receptor.

Soluble receptors or other soluble binding molecules are identified in a similar manner. Labeled TMEC is incubated with extracts or other appropriate materials derived from activated or inflamed tissues such as TMLR. After incubation, TMEC complexes (which are larger than the size of the purified chemokine molecule) are identified by a sizing technique such as size exclusion chromatography or density gradient centrifugation and are purified by methods known in the art. The soluble receptors or binding protein(s) are subjected to N-terminal sequencing to obtain information sufficient for database identification, if the soluble protein is known, or for cloning, if the soluble protein is unknown.

XVI Use and Administration of TMEC

Antibodies, inhibitors, receptors or antagonists of TMEC (or other treatments for excessive chemokine production, hereinafter abbreviated TEC), can provide different effects when administered therapeutically. TECs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, receptor or antagonist being formulated and the condition to be treated. Characteristics of TEC include solubility of the molecule, half-life and antigenicity/ immunogenicity; these and other characteristics may aid in defining an effective carrier. Native human proteins are preferred as TECs, but organic or synthetic molecules resulting from drug screens may be equally effective in particular situations.

TECs may be delivered by known routes of administration including but not limited to topical creams and gels; transmucosal spray and aerosol, transdermal patch and bandage; injectable, intravenous and lavage formulations; and orally administered liquids and pills, particularly formulated to resist stomach acid and enzymes. The particular formulation, exact dosage, and route of administration will be determined by the attending physician and will vary according to each specific situation.

Such determinations are made by considering multiple variables such as the condition to be treated, the TEC to be administered, and the pharmacokinetic profile of the particular TEC. Additional factors which may be taken into account include the disease state (e.g. severity), age, weight, gender, diet, time of administration, drug combination, reaction sensitivities, and tolerance/response to therapy. Long acting TEC formulations might be administered every 3 to 4 days, every week, or once every two weeks depending on half-life and clearance rate of the particular TEC.

Normal dosage amounts may vary from 0.1 to 100,000 micrograms, up to a total dose of about 1 g, depending upon the route of administration. Guidance as to particular dosages and methods of delivery is provided in the literature; see U.S. Pat. No. 4,657,760; 5,206,344; or 5,225,212. It is anticipated that different formulations will be effective for different TECs and that administration targeting the inflamed or diseased tissue may necessitate delivery in a manner different from that to another organ or tissue.

It is contemplated that conditions or diseases which specifically activate lymphocytes or other leukocytes may precipitate damage that is treatable with TECs. Such conditions or diseases may be specifically diagnosed by the tests discussed above, and such testing should be performed in suspected cases of viral, bacterial, fungal or parasitic infections; mechanical injury associated with trauma; autoimmune or hereditary diseases such as AIDS, allergies, asthma and rheumatoid arthritis; cancers and infiltrative diseases such as carcinomas, leukemias and lymphomas; or other physiologic and pathologic problems associated with uncontrolled proliferation of T lymphocytes.

All publications and patents mentioned in the above specification are herein incorporated by reference. The foregoing written specification is considered to be sufficient to enable one skilled in the art to practice the invention. Indeed, various modifications of the above described modes for carrying out the invention which are readily apparent to those skilled in the field of molecular biology or related fields are intended to be within the scope of the following claims.

We claim:

1. An isolated and purified polynucleotide consisting of the nucleic acid sequence of SEQ ID NO:1.

2. An expression vector comprising the polynucleotide of claim 1.

3. A host cell transformed with the expression vector of claim 2.

4. A method for producing T cell mixed lymphocyte reaction expressed chemokine polypeptide, said method comprising the steps of:
   a) culturing the host cell of claim 3 under conditions suitable for the expression of the polypeptide; and
   b) recovering the polypeptide from the host cell culture.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
  ( A ) LENGTH: 768 base pairs
  ( B ) TYPE: nucleic acid
  ( C ) STRANDEDNESS: single
  ( D ) TOPOLOGY: linear ( i i ) MOLECULE TYPE: cDNA ( v i i ) IMMEDIATE SOURCE:
  ( A ) LIBRARY: TMLR
  ( B ) CLONE: 292810

( x i ) SEQUENCE DESCRIPTION: SEQ ID NO:1:

| | | | | | |
|---|---|---|---|---|---|
| GGCCACAAGG | CGATAGGTTA | GTATGAACAG | GGAAAGGGAC | ATTTTTTTTT | TTTAAGAAAA | 60 |
| ATAAAAGCAT | CAGTATTGCA | AAGACTTTCC | ATGATCCTAT | ACCCACCTCG | AAAGCCCCCT | 120 |
| CTCACCACAG | GAAGTGCACT | GACCATTGGA | GGCATAAAAG | AGATCCTCAA | AGAGCCCGAT | 180 |
| CCTCACTCTC | CCTGCACAGC | TCAGCGGGAC | CTCAGCCATG | AGACTTCTCA | TCCTGGCCCT | 240 |
| CCTTGGCATC | TGCTCTCTCA | CTGCATACAT | TGTGGAAGGT | GTAGGGAGTG | AAGTCTCACA | 300 |
| TAGGAGGACC | TGTGTGAGCC | TCACTACCCA | GCGACTGCCA | GTTAGCAGAA | TCAAGACCTA | 360 |
| CACCATCACG | GAAGGCTCCT | TGAGAGCAGT | AATTTTTATT | ACCAAACGTG | GCCTAAAAGT | 420 |
| CTGTGCTGAT | CCACAAGCCA | CGTGGGTGAG | AGACGTGGTC | AGGAGCATGG | ACAGGAAATC | 480 |
| CAACACCAGA | ATAACATGA | TCCAGACCAA | GCCAACAGGA | ACCCAGCAAT | CGACCAATAC | 540 |
| AGCTGTGACC | CTGACTGGCT | AGTAGTCTCT | GGCACCCTGT | CCGTCTCCAG | CCAGCCAGCT | 600 |
| CATTTCACTT | TACACCCTCA | TGGACTGAGA | TTATACTCAC | CTTTTATGAA | AGCACTGCAT | 660 |
| GAATAAAATT | ATTCCTTTGT | ATTTTACTT | TTAAATGTCT | TCTGTATTCA | CTTATATGTT | 720 |
| CTAATTAATA | AATTATTTAT | TATTAAGAAT | AAAAAAAAAA | AAAAAAA | | 768 |

( 2 ) INFORMATION FOR SEQ ID NO:2:

( i ) SEQUENCE CHARACTERISTICS:
  ( A ) LENGTH: 114 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Arg | Leu | Leu | Ile | Leu | Ala | Leu | Leu | Gly | Ile | Cys | Ser | Leu | Thr | Ala |
| 1 | | | | 5 | | | | | 10 | | | | | 15 | |
| Tyr | Ile | Val | Glu | Gly | Val | Gly | Ser | Glu | Val | Ser | His | Arg | Arg | Thr | Cys |
| | | | 20 | | | | | 25 | | | | | 30 | | |
| Val | Ser | Leu | Thr | Thr | Gln | Arg | Leu | Pro | Val | Ser | Arg | Ile | Lys | Thr | Tyr |
| | | | 35 | | | | 40 | | | | | 45 | | | |
| Thr | Ile | Thr | Glu | Gly | Ser | Leu | Arg | Ala | Val | Ile | Phe | Ile | Thr | Lys | Arg |
| | 50 | | | | | 55 | | | | | 60 | | | | |
| Gly | Leu | Lys | Val | Cys | Ala | Asp | Pro | Gln | Ala | Thr | Trp | Val | Arg | Asp | Val |
| 65 | | | | | 70 | | | | | 75 | | | | | 80 |
| Val | Arg | Ser | Met | Asp | Arg | Lys | Ser | Asn | Thr | Arg | Asn | Asn | Met | Ile | Gln |
| | | | | 85 | | | | | 90 | | | | | 95 | |
| Thr | Lys | Pro | Thr | Gly | Thr | Gln | Gln | Ser | Thr | Asn | Thr | Ala | Val | Thr | Leu |
| | | | 100 | | | | | 105 | | | | | 110 | | |
| Thr | Gly | | | | | | | | | | | | | | |
| | 114 | | | | | | | | | | | | | | |